(12) United States Patent
Wan et al.

(10) Patent No.: US 11,656,211 B2
(45) Date of Patent: May 23, 2023

(54) SYSTEMS AND METHODS FOR IDENTIFYING GAS MIGRATION USING HELIUM

(71) Applicant: Saudi Arabian Oil Company, Dhahran (SA)

(72) Inventors: Zhenzhu Wan, Dhahran (SA); Khaled Arouri, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 142 days.

(21) Appl. No.: 17/026,717

(22) Filed: Sep. 21, 2020

(65) Prior Publication Data

US 2022/0091082 A1 Mar. 24, 2022

(51) Int. Cl.
*G01N 33/00* (2006.01)
*E21B 47/10* (2012.01)
(Continued)

(52) U.S. Cl.
CPC ......... *G01N 33/0031* (2013.01); *E21B 47/10* (2013.01); *E21B 49/0875* (2020.05); *G01N 33/0075* (2013.01)

(58) Field of Classification Search
CPC ............ G01N 33/0031; G01N 33/0075; E21B 47/10; E21B 49/0875; G01V 9/007
See application file for complete search history.

(56) References Cited

U.S. PATENT DOCUMENTS 5,246,860 A 9/1993 Hutchins et al.
5,501,273 A 3/1996 Puri
(Continued)

FOREIGN PATENT DOCUMENTS

CN 109387540 A 2/2019
EP 414564 A2 2/1991

OTHER PUBLICATIONS

Ballentine et al., "The use of natural He, Ne and Ar isotopes to study hydrocarbon-related fluid provenance, migration and mass balance in sedimentary basins", Geofluids: Origin, Migration and Evolution of Fluids in Sedimentary Basins, Geological Society Special Publication No. 78, pp. 347-361, 1994.

(Continued)

*Primary Examiner* — Herbert K Roberts
*Assistant Examiner* — Anthony W Megna Fuentes
(74) *Attorney, Agent, or Firm* — Dinsmore & Shohl LLP

(57) ABSTRACT

A system for identifying migration direction of natural gases is provided and may include a network of $^4$He gas sensors and a migration monitoring hub. The network of $^4$He gas sensors may be operable to identify a $^4$He concentration in gas samples. The migration monitoring hub may be in communication with the network of $^4$He gas sensors and may comprise a user interface and a processor. The processor may be operable to determine a direction of increasing $^4$He concentration and map increasing $^4$He concentration. The user interface may be operable to display migration information. A method for identifying migration direction of natural gases is also provided and may include isolating a target portion of a petroleum exploration environment, detecting gas samples from a network of $^4$He gas sensors, identifying a $^4$He concentration in the gas samples, and determining a direction of increasing $^4$He concentration in the gas samples.

9 Claims, 3 Drawing Sheets

(51) Int. Cl.
*E21B 49/08* (2006.01)
*G01V 9/00* (2006.01)

(56) References Cited

U.S. PATENT DOCUMENTS

| | | | |
|---|---|---|---|
| 5,672,827 A | 9/1997 | Jursich | |
| 7,294,172 B2 | 11/2007 | Baksh et al. | |
| 8,215,164 B1 | 7/2012 | Hussain et al. | |
| 8,775,087 B1 * | 7/2014 | Selman | G01V 11/002 702/9 |
| 9,810,064 B2 | 11/2017 | Garcia | |
| 10,527,601 B2 | 1/2020 | Dreyfus et al. | |
| 2006/0090546 A1 * | 5/2006 | McCoy | G01M 3/226 73/40.7 |
| 2011/0231099 A1 * | 9/2011 | Elkins | E21B 49/08 374/E7.004 |
| 2011/0277996 A1 | 11/2011 | Cullick et al. | |
| 2012/0134749 A1 | 5/2012 | Darrah | |

OTHER PUBLICATIONS

Barry et al., "Noble gases solubility models of hydrocarbon charge mechanism in the Sleipner Vest gas field", Geochimica et Cosmochimica Acta, vol. 194, pp. 291-309, 2016.

Byrne et al., "Noble gases in conventional and unconventional petroleum systems", Geological Society London Special Publications, 23 pgs., 2017.

Cao et al., "Noble gas isotopic variations and geological implication of Longmaxi shale gas in Sichuan Basin, China", Marine and Petroleum Geology, pp. 1-9, 2017.

Clarke et al., "Determination of Tritium by Mass Spectrometric Measurement of He", International Journal of Applied Radiation and Isotopes, vol. 27, pp. 515-522, 1976.

Craig et al., "Primordial Neon, Helium, and Hydrogen in Oceanic Basalts", Earth and Planetary Science Letters, vol. 31, pp. 369-385, 1976.

Ni et al., "Helium signatures of gases from the Sichuan Basin, China", Organic Geochemistry, vol. 74, pp. 33-43, 2014.

Ozima et al., "Noble Gas Geochemistry", Cambridge University Press, 302 pgs., 2004.

Prinzhofer, "Noble Gas in Oil and Gas Accumulations", The Noble Gases as Geochemical Tracers, Advances in Isotope Cheochemistry, DOI: 10.1007/978-3-642-28836-4_9,Springer-Verlag Berlin Heidelberg, pp. 225-247, 2013.

Zhang et al., "Molecular and carbon isotopic variation in 3.5 years shale gas production from Longmaxi Formation in Sichuan Basin, China", Marine and Petroleum Geology, vol. 89, pp. 27-37, 2018.

International Search Report and Written Opinion dated Jun. 9, 2021 pertaining to International application No. PCT/US2020/066384 filed Dec. 21, 2020, 15 pages.

Prinzhofer, A. et al. "Gas Isotopes Tracing: an Important Tool for Hydrocarbons Exploration", Oil & Gas Science & Technology: Revue De L'Institut Francais Du Petrole, Editions Techn IP Paris, FR, vol. 58, No. 2, Jan. 1, 2003, pp. 299-311.

Cecconi, B. et al. "Helium Detection at Wellsite: A Powerful Geochemical Tool", Offshore Mediterranean Conference and Exhibition, Mar. 29, 2017 Retrieved from the Internet: URL:https://onepetro.org/OMCONF/proceeding s/OMC17/All-OMC17/OMC-2017-814/1872 [retrieved on May 26, 2021], pp. 1-10.

\* cited by examiner

SYSTEMS AND METHODS FOR IDENTIFYING GAS MIGRATION USING HELIUM

BACKGROUND

The present disclosure relates generally to gas migration and, more specifically, to identifying natural gas migration direction via a noble gas.

BRIEF SUMMARY

According to the subject matter of the present disclosure, a system for identifying migration direction of natural gases from source to reservoir in a petroleum exploration environment may comprise a network of $^4$He gas sensors and a migration monitoring hub. The network of $^4$He gas sensors may be positioned at a plurality of reservoir wells in the petroleum exploration environment and may be operable to identify a $^4$He concentration in gas samples at the reservoir wells. The migration monitoring hub may be in communication with the network of $^4$He gas sensors and may comprise a user interface and a processor in communication with the network of $^4$He gas sensors. The processor may be operable to determine a direction of increasing $^4$He concentration between selected ones of the reservoir wells based on the identified $^4$He concentration at the reservoir wells and map increasing $^4$He concentration in the petroleum exploration environment based on the direction of increasing $^4$He concentration between selected ones of the reservoir wells. The user interface may be in communication with the processor and may be operable to display migration information based on the mapped increasing $^4$He concentration in the petroleum exploration environment.

In accordance with one embodiment of the present disclosure, a method for identifying migration direction of natural gases from source to reservoir in a petroleum exploration environment may comprise isolating a target portion of the petroleum exploration environment, detecting gas samples from a network of $^4$He gas sensors positioned at a plurality of reservoir wells in the target portion of the petroleum exploration environment, identifying a $^4$He concentration in the gas samples at the plurality of reservoir wells, and determining a direction of increasing $^4$He concentration in the gas samples between the plurality of wells in the target portion of the petroleum exploration environment.

Although the concepts of the present disclosure are described herein with primary reference to natural gas, it is contemplated that the concepts will enjoy applicability to any hydrocarbon. For example, and not by way of limitation, it is contemplated that the concepts of the present disclosure will enjoy applicability to oil such as, but not limited to, crude oil.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
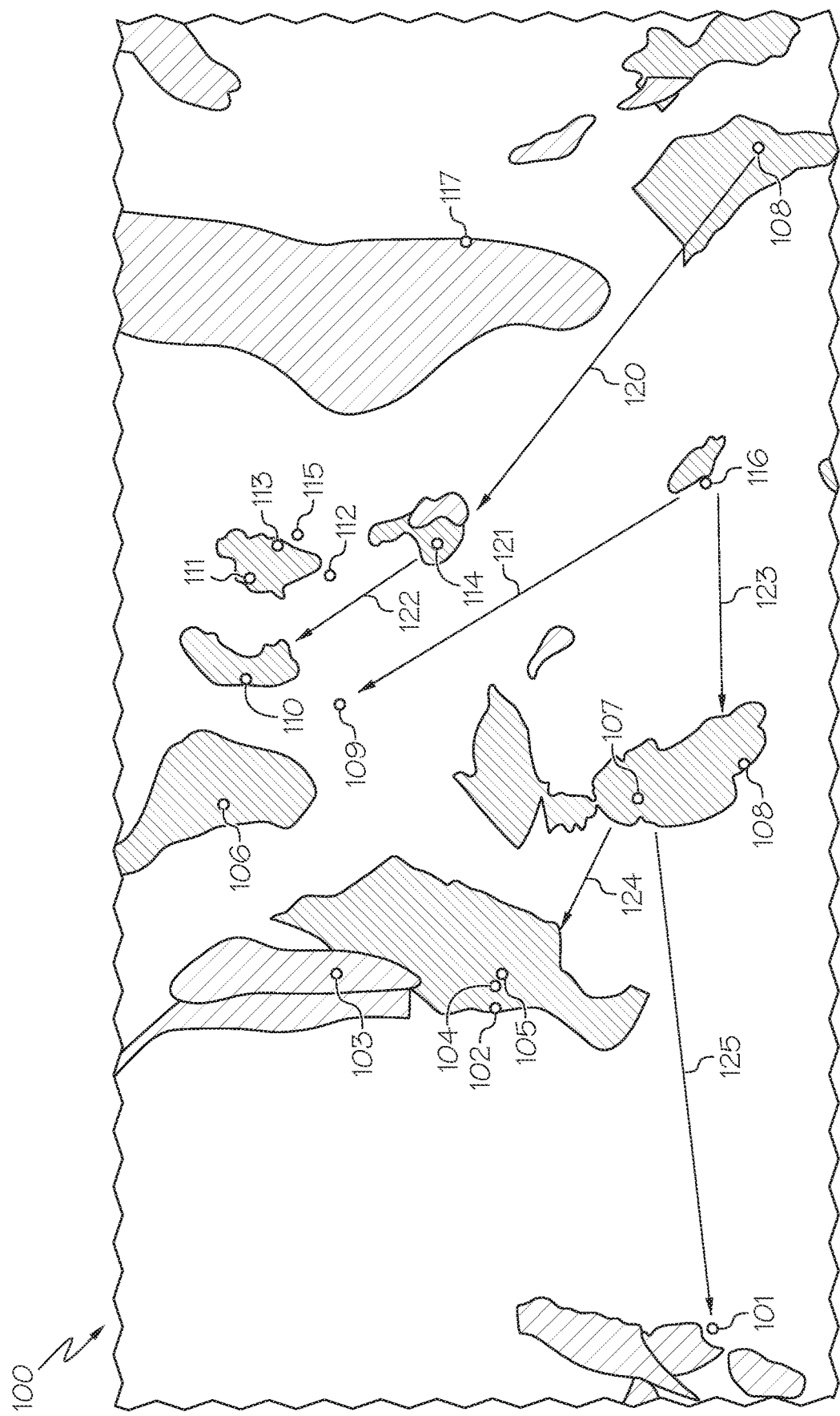
FIG. 1 schematically depicts a user interface in accordance with one or more embodiments of the present disclosure.

During the formation of gases, gases that are produced in source rocks migrate to reservoirs within petroleum exploration environments. The migration of gases in petroleum exploration environments is a little-understood process of the petroleum system. However, the migration of gases is also a critical process in the petroleum system. While efforts have been made to better understand the migration of gases from source rock to reservoir, few, if any, methods have proven to be consistent and verifiable. An identification of the migration of gases may prove valuable for assessing hydrocarbon origin, hydrocarbon characteristics, and reserves in potential petroleum exploration environments. Accordingly, there is an ongoing need for identifying the migration of gases from source rock to reservoir.

The migration of gases from source rock in petroleum exploration environments may include both primary migration and secondary migration. Primary migration may include the expulsion of the gases from a fine-grained source rock to a coarse-grained carrier bed, while secondary migration may include the passage of gasses from the coarse-grained carrier bed to a reservoir in the petroleum exploration environment. Occasionally, the migration of gases may include tertiary migration, which occurs when the gases migrate from a first reservoir to a second reservoir.

Natural gas production may span a certain geological time, for example, from $t_1$ to $t_3$, During production, the production rate may increase quickly between $t_1$ and $t_2$, where $t_2$ is somewhere between $t_1$ and $t_3$. The production rate may then decrease increase between $t_2$ and $t_3$.

The present inventors have identified that noble gases such as, but not limited to, helium may be used as an identifier of gas migration. Helium is highly inert and may generally be immune to subsurface geochemical reactions that may occur during migration from source rock to reservoir. Additionally, helium is readily detectable and may be measured at low concentrations (e.g., a few parts per million (ppm)). While there are nine helium isotopes, there are only two stable helium isotopes, $^3$He and $^4$He. These helium isotopes may be distributed mainly in the atmosphere, the water, the crust, and the mantle. In each of the atmosphere, the water, the crust, and the mantle, $^3$He and $^4$He comprise different concentrations and ratios. For example, in the atmosphere, the helium concentration may be about 5.24 ppm, 99.99986% of which may be $^4$He, and the rest (0.00014%) may be $^3$He. Additionally, the ratio of $^3$He/$^4$He in the atmosphere may be about $4 \times 10^{-4}$. In the crust, the helium concentration may be about 8 ppb. Accordingly, helium concentration and stable isotopic ratio ($^3$He/$^4$He) may indicate the origin of the helium gas.

In the crust, $^4$He gas may be predominantly radiogenic. That is, the $^4$He gas may be a product of alpha decay of radioactive elements such as, but not limited to, Uranium (U) and Thorium (Th). The production rate per gram of specimen $^4$He gas that originates from the crust may be calculated using Equations (1) and (2), where P is the production rate (measured in cubic centimeters at standard temperature and pressure per gram per year) and U and Th are the concentrations of Uranium and Thorium, respectively (measured in parts per million):

$$P(^4He) = 0.2355 \times 10^{-12} U^* \quad \text{Equation (1)}$$

$$U^* = U\left\{1 + 0.123\left(\frac{Th}{U-4}\right)\right\} \quad \text{Equation (2)}$$

Similar to the natural gas, $^4$He gas production may span a certain geological time. However, the production rate of $^4$He gas may generally be fixed and slows marginally as the radioactive elements continue to decay. In-situ curst-derived $^4$He gas may be absorbed onto mineral grains or dissolved in water. Moving fluids, such as water, gas, and oil may pick up noble gases from their sources, along their migration pathways, and carry the noble gases to their reservoirs where the fluids may accumulate.

In addition to crust-derived helium produced through radioactive decay, atmospheric helium may also end up in the crust. The atmospheric helium may be carried by meteoric water in aquifers. However, there is usually little atmospheric helium observed in the crust. In fact, atmospheric helium is typically only observed in the top few meters of the subsurface.

Figure 2:
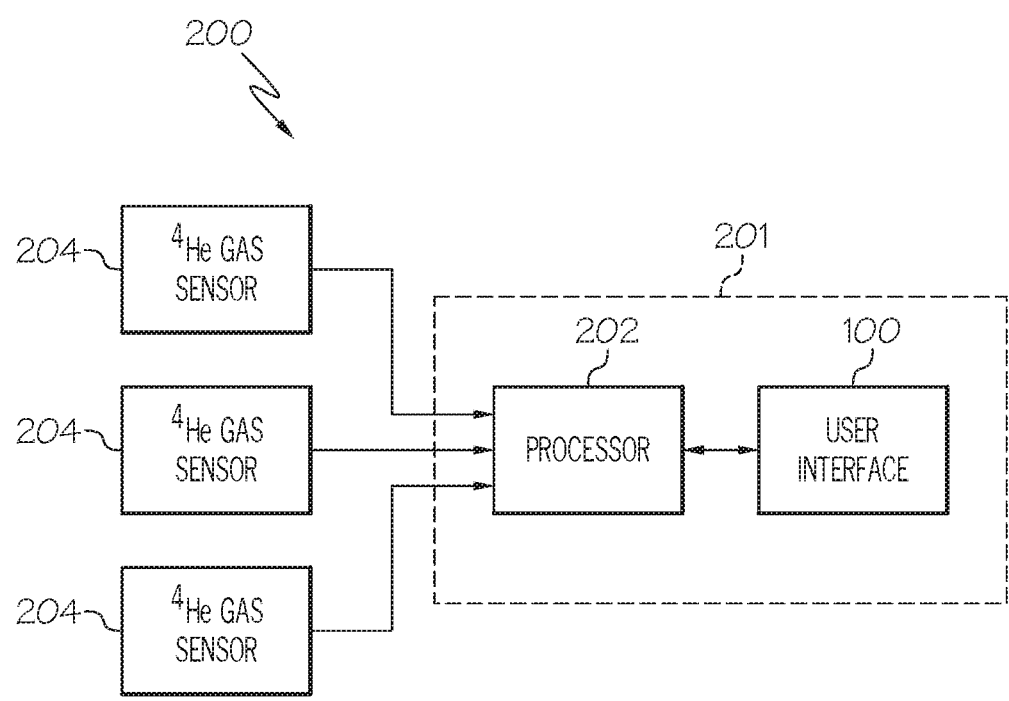
FIG. 2 schematically depicts a network of $^4$He gas sensors and a migration monitoring hub in accordance with one or more embodiments of the present disclosure.

Referring initially to FIGS. 1 and 2, a system 200 for identifying migration direction of natural gases from source to reservoir in a petroleum exploration environment may comprise a network of $^4$He gas sensors 204 and a migration monitoring hub 201. FIG. 1 illustrates the user interface 100 of the migration monitoring hub 201, while FIG. 2 schematically depicts a network of $^4$He gas sensors 204 and the migration monitoring hub 201. The user interface 100 of FIG. 1 illustrates a plurality of reservoir wells 101-118 and migration lines 120-125 identifying the migration direction of natural gases from source to reservoir in the petroleum exploration environment.

Referring again to FIGS. 1 2, and 3, the network of $^4$He gas sensors 204 may be positioned at a plurality of reservoir wells 300 in the petroleum exploration environment and may be operable to identify a $^4$He concentration in gas samples at the reservoir wells 300. Referring now to FIG. 2, the migration monitoring hub 201 may be in communication with the network of $^4$He gas sensors 204 and may comprise a user interface 100 and a processor 202 in communication with the network of $^4$He gas sensors 204. The processor 202 may be operable to determine a direction of increasing $^4$He concentration between selected ones of the reservoir wells 300 based on the identified $^4$He concentration at the reservoir wells 300 and map increasing $^4$He concentration in the petroleum exploration environment based on the direction of increasing $^4$He concentration between selected ones of the reservoir wells 300. The user interface 100 may be in communication with the processor 202 and may be operable to display migration information based on the mapped increasing $^4$He concentration in the petroleum exploration environment.

In the system 200, the natural gases may comprise both hydrocarbons and helium, as helium may serve as a migration identifier, as detailed above. According to one or more embodiments, the petroleum exploration environment and the natural gases may be free of helium injection. As used throughout the present disclosure, "helium injection" may refer to the introduction of any additional helium, i.e., helium that is not naturally produced through radioactive decay or cosmogenic helium that is introduced to the petroleum exploration environment via, for example, meteoric water.

Figure 3:
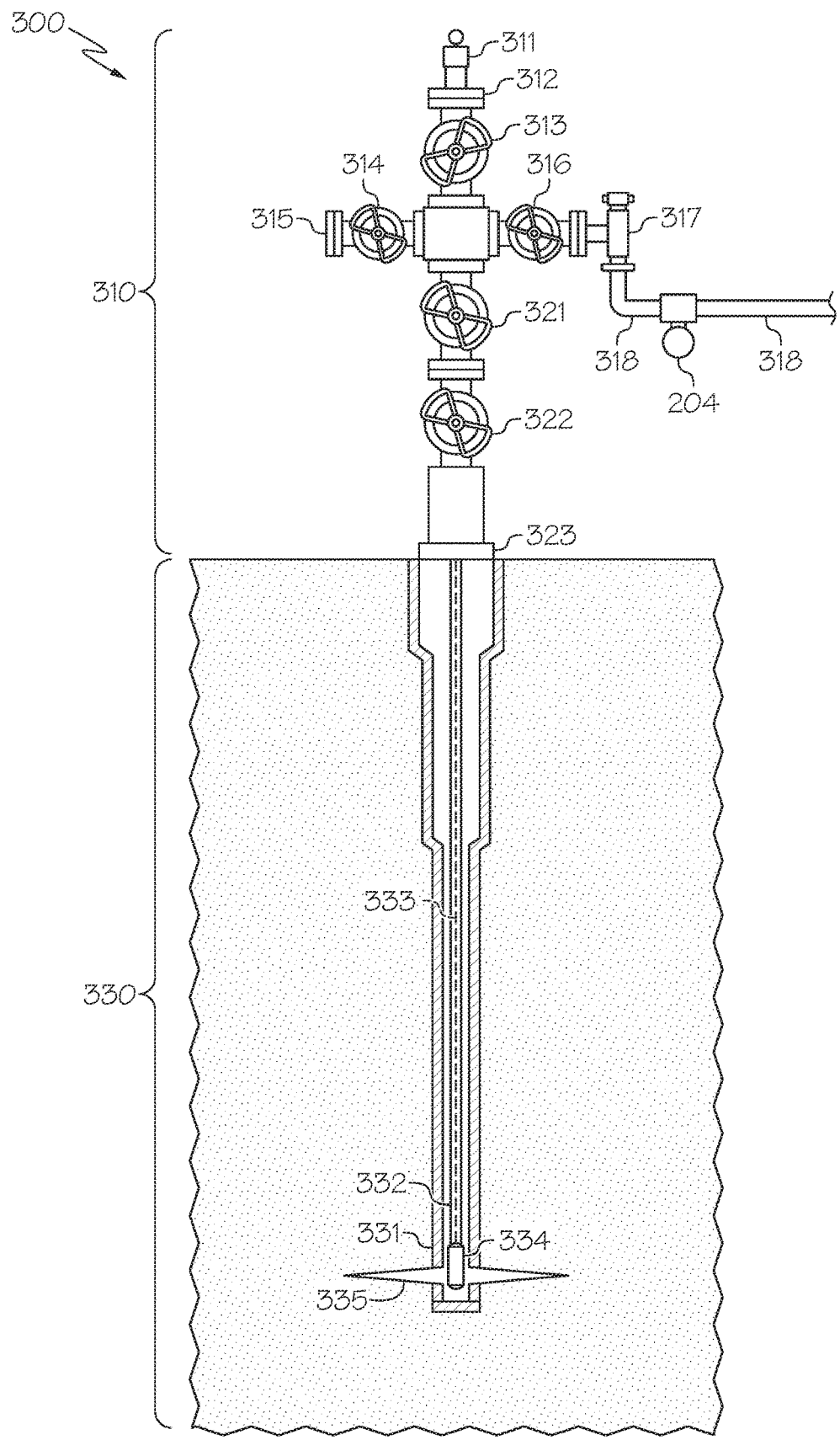
FIG. 3 schematically depicts a reservoir well in accordance with one or more embodiments of the present disclosure.

Referring to FIGS. 1 and 3, the $^4$He gas sensors 204 may identify the $^4$He concentration in gas samples in production flow lines at the plurality of reservoir wells 300. According to one or more embodiments, the reservoir wells 300 may be in fluid communication with dedicated fluid control trees. The dedicated fluid control trees may be in fluid communication with corresponding production flow lines. The $^4$He gas sensors 204 may be configured to identify $^4$He concentrations in the production flow lines in fluid communication with the dedicated fluid control trees. The $^4$He gas sensors 204 may be operable to detect $^4$He concentration in the gas samples that may be consistent with levels of radiogenic helium. According to one or more embodiments, the $^4$He gas sensors 204 may be operable to detect $^4$He concentration in an amount of less than 10 ppm. In embodiments, the $^4$He gas sensors 204 may be operable to detect $^4$He concentration in the gas samples in a range from 1 ppm to 3,000 ppm. For example, the $^4$He gas sensors 204 may be operable to detect $^4$He concentration in the gas samples in a range from 10 ppm to 2,500 ppm.

According to one or more embodiments, the $^4$He gas sensors 204 may identify the $^4$He concentration in gas samples in real time. That is, the $^4$He gas sensors 204 may identify the $^4$He concentration in gas samples in production flow lines at the plurality of reservoir wells 300 in real time. As used throughout the present disclosure, "real time" may refer to an instantaneous reading, such that the gas samples do not need further testing or analysis to determine the $^4$He concentration.

Referring again to FIG. 1-2, the communication between migration monitoring hub 201 and the $^4$He gas sensors 204 enables the migration monitoring hub 201 to gather, collect, receive, or otherwise process $^4$He concentration generated by the network of $^4$He gas sensors 204. Similarly, the communication between the user interface 100, which may comprise, for example, a touch screen input/output (I/O) device, or any type of conventional or yet to be developed visual display and I/O device, enables the user interface 100 to gather, collect, receive, or otherwise process, mapped $^4$He concentration data for manipulation and display According to one or more embodiments, the user interface 100 of the migration monitoring hub 201 may comprise prompts configured to allow a user to select certain ones of the network of $^4$He gas sensors 204 for the processor 202 to consider in mapping increasing $^4$He concentration in the petroleum exploration environment. In embodiments, the user may selectively choose individual $^4$He gas sensors 204 to be considered. The user may focus on a specific area within the petroleum exploration environment by selecting a few local $^4$He gas sensors 204. Alternatively, the user may focus on the petroleum exploration environment as a whole on a more global level.

Referring again to FIG. 1, as previously detailed, the user interface 100 may be operable to display migration information. According to one or more embodiments, the migration information may comprise migration trends. Migration trends may include the path (i.e., the direction) that the natural gases follow from source rock to reservoir. The migration information may provide a better understanding of the migration of the natural gas.

Referring now to FIG. 3, one embodiment of a reservoir well 300 is schematically depicted. It should be noted that other types and configurations of reservoir wells 300 are contemplated and that FIG. 3 is an example of just one type and configuration of a reservoir well 300 that may be used with the embodiments described herein. The reservoir well 300 may comprise a fluid control tree 310 of the reservoir well 300 that may be above the surface, and a subsurface portion 330 of the reservoir well 300.

The fluid control tree 310 may generally comprise a number of valves, spools, and fittings that regulate and control the flow of pipes in a reservoir well 300. As seen in FIG. 3, the fluid control tree 310 may comprise a tree cap 311, a tree adapter 312, a swab valve 313, a kill wing valve 314, a kill wing connection 315, a production wing valve 316, a surface choke 317, a production line 318, the $^4$He gas sensor 204, an upper master valve 321, a lower master valve 322, and a tubing head adapter 323.

The fluid control tree 310 may be in fluid communication with a casing 331. A production tubing 332 may also be in fluid communication with the fluid control tree 310 and may be positioned within an annular space of the casing 331. A rod string 333 may be connected to a production pump 334. The production pump 334 may be operable to direct natural gases from the reservoir to the surface via the production tubing 332. The production pump 334 may direct natural gases from the reservoir to the reservoir well 300 via casing perforations 335, which may fluidly connect the reservoir to the reservoir well 300.

In another embodiment, a method for identifying migration direction of natural gases from source to reservoir in a petroleum exploration environment may comprise isolating a target portion of the petroleum exploration environment from helium injection, detecting gas samples from a network of $^4$He gas sensors 204 positioned at a plurality of reservoir wells 300 in the target portion of the petroleum exploration environment, identifying a $^4$He concentration in the gas samples at the plurality of reservoir wells 300, determining a direction of increasing $^4$He concentration in the gas samples between the plurality of wells in the target portion of the petroleum exploration environment, and mapping an increase of $^4$He concentration in the target portion of the petroleum exploration environment. It is noted that an environment where a statistically insignificant amount of helium is injected may still be considered as isolated from helium injection.

According to one or more embodiments, identifying the $^4$He concentration in the gas samples may comprise $^4$He gas sensors identifying $^4$He concentrations in production flow lines at the plurality of reservoir wells 101. It is contemplated that identifying the $^4$He concentration in the gas samples may comprise identifying the $^4$He concentration in gas samples in real time.

According to one or more embodiments, the method may further comprise displaying migration information based on increasing $^4$He concentration in the petroleum exploration environment on a user interface 100. Additionally, the method may further comprise identifying migration information comprising migration trends, compound compositions, isotopic compositions, or combinations thereof.

In preparing the user interface schematically depicted in FIG. 1, gas samples were obtained from an Aeolian sandstone reservoir. In the gas samples, the $^3$He/$^4$He ratio ranged from 1.5-4.4×10$^{-8}$. As the atmospheric $^3$He/$^4$He ratio may be about 1.384×10$^{-6}$, cosmogenic and radiogenic $^3$He/$^4$He ratios are 4×10$^{-4}$ and 1×10$^{-8}$, respectively. Therefore, it can be concluded that the helium in the gas samples is about 99% radiogenic helium. As shown in Table 1, $^4$He concentrations were measured at a plurality of reservoir wells, 101-118.

TABLE 1

| Reservoir Well | $^4$He Concentration (ppm) |
|---|---|
| 101 | 923 |
| 102 | 607 |
| 103 | 533 |
| 104 | 847 |
| 105 | 719 |
| 106 | 462 |
| 107 | 485 |
| 108 | 642 |
| 109 | 523 |
| 110 | 549 |
| 111 | 349 |
| 112 | 321 |
| 113 | 376 |
| 114 | 442 |
| 115 | 322 |
| 116 | 488 |
| 117 | 626 |
| 118 | 394 |

Still referring to FIG. 1, once the $^4$He concentrations were measured at the plurality of reservoir wells, the processor identified migration direction of the natural gas by way of increasing $^4$He concentrations and displayed on the user interface. Migration lines 120-125 show the general migration direction of the natural gases, as determined by increasing $^4$He concentration in the gas samples obtained at the plurality of reservoir wells.

It is noted that recitations herein of a component of the present disclosure being "configured" or "programmed" in a particular way, to embody a particular property, or to function in a particular manner, are structural recitations, as opposed to recitations of intended use. More specifically, the references herein to the manner in which a component is "configured" or "programmed" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A system for identifying migration direction of natural gases from source to reservoir in a petroleum exploration environment, the system comprising a network of $^4$He gas sensors and a migration monitoring hub, wherein:
the network of $^4$He gas sensors are positioned at a plurality of reservoir wells in the petroleum exploration environment and are operable to detect $^4$He concentration in gas samples at the reservoir wells in a range consistent with levels of radiogenic helium in the gas samples from 10 ppm to 2,500 ppm;
the migration monitoring hub is in communication with the network of $^4$He gas sensors and comprises a user interface and a processor in communication with the network of $^4$He gas sensors;
the communication between the migration monitoring hub and the $^4$He gas sensors enables the migration monitoring hub to process mapped $^4$He concentration data for manipulation and display at the user interface;
the processor is operable to determine a direction of increasing $^4$He concentration between selected ones of the reservoir wells based on the detected $^4$He concentration at the reservoir wells and map increasing $^4$He concentration in the petroleum exploration environment based on the direction of increasing $^4$He concentration between selected ones of the reservoir wells;
the user interface is in communication with the processor, wherein the user interface comprises an input/output device for manipulating and displaying mapped $^4$He concentration data, and illustrates the plurality of reservoir wells comprising individual $^4$He gas sensors, migration lines identifying the migration direction of natural gases from source to reservoir in the petroleum exploration environment, and the increasing $^4$He concentration in the petroleum exploration environment, as determined by the processor; and
the user interface of the migration monitoring hub comprises prompts that are configured to allow a user to select certain ones of the network of $^4$He gas sensors for the processor to consider in mapping increasing $^4$He concentration in the petroleum exploration environment such that a specific area is focused on within the petroleum exploration environment by selectively choosing individual $^4$He gas sensors to be considered by the processor.

2. The system of claim 1, wherein the $^4$He gas sensors detect the $^4$He concentration in gas samples in production flow lines at the plurality of reservoir wells.

3. The system of claim 1, wherein: the reservoir wells are in fluid communication with dedicated fluid control trees; the dedicated fluid control trees are in fluid communication with corresponding production flow lines; and the $^4$He gas sensors are configured to detect $^4$He concentrations in the production flow lines in fluid communication with the dedicated fluid control trees.

4. The system of claim 3, wherein the $^4$He gas sensors detect the $^4$He concentration in gas samples in real time.

5. The system of claim 1, wherein the $^4$He gas sensors detect the $^4$He concentration in gas samples in real time.

6. The system of claim 1, wherein the migration information comprises migration trends.

7. A method for identifying migration direction of natural gases from source to reservoir in a petroleum exploration environment utilizing a system comprising a network of $^4$He gas sensors and a migration monitoring hub, wherein:
the network of $^4$He gas sensors are positioned at a plurality of reservoir wells in the petroleum exploration environment and are operable to detect $^4$He concentration in gas samples at the reservoir wells in a range consistent with levels of radiogenic helium in the gas samples from 10 ppm to 2,500 ppm;
the migration monitoring hub is in communication with the network of $^4$He gas sensors and comprises a user interface and a processor in communication with the network of $^4$He gas sensors;
the communication between the migration monitoring hub and the $^4$He gas sensors enables the migration monitoring hub to process mapped $^4$He concentration data for manipulation and display at the user interface;
the processor is operable to determine a direction of increasing $^4$He concentration between selected ones of the reservoir wells based on the detected $^4$He concentration at the reservoir wells and map increasing $^4$He concentration in the petroleum exploration environment based on the direction of increasing $^4$He concentration between selected ones of the reservoir wells;
the user interface is in communication with the processor, wherein the user interface comprises an input/output device for manipulating and displaying mapped $^4$He concentration data, and illustrates the plurality of reservoir wells comprising individual $^4$He gas sensors, migration lines identifying the migration direction of natural gases from source to reservoir in the petroleum exploration environment, and the increasing $^4$He concentration in the petroleum exploration environment, as determined by the processor;
the user interface of the migration monitoring hub comprises prompts that are configured to allow a user to select certain ones of the network of $^4$He gas sensors for the processor to consider in mapping increasing $^4$He concentration in the petroleum exploration environment such that a specific area is focused on within the petroleum exploration environment by selectively choosing individual $^4$He gas sensors to be considered by the processor; and
the method comprises:
detecting gas samples from a network of $^4$He gas sensors positioned at a plurality of reservoir wells in the petroleum exploration environment;
isolating a target portion of the petroleum exploration environment using the prompts of the user interface to select certain ones of the network of $^4$He gas sensors for the processor to consider in mapping increasing $^4$He concentration in the petroleum exploration environment and focus on a specific area within the petroleum exploration environment;
detecting a $^4$He concentration in the gas samples at selectively chosen individual ones of the $^4$He gas sensors at the plurality of reservoir wells; and
determining a direction of increasing $^4$He concentration in the gas samples between the plurality of wells in the target portion of the petroleum exploration environment.

8. The method of claim 7, further comprising displaying migration information based on increasing $^4$He concentration in the petroleum exploration environment on the user interface.

9. The method of claim 7, further comprising identifying migration information comprising migration trends.

\* \* \* \* \*